United States Patent [19]

Goralski et al.

[11] 4,141,916
[45] Feb. 27, 1979

[54] 3,4,5-TRICHLORO-N,N-DI(LOWERALKYL)-2-((CHLOROMETHYL)THIO)BENZENESULFONAMIDES

[75] Inventors: Christian T. Goralski, Midland; George A. Burk, Bay City, both of Mich.

[73] Assignee: The Dow Chemical Company, Midland, Mich.

[21] Appl. No.: 877,059

[22] Filed: Feb. 13, 1978

[51] Int. Cl.² .................................. C07C 143/78
[52] U.S. Cl. ................................... 260/556 AR
[58] Field of Search ......................... 260/556 AR

[56] References Cited

U.S. PATENT DOCUMENTS

| | | | |
|---|---|---|---|
| 3,574,739 | 4/1971 | Wei et al. | 260/556 AR |
| 3,828,078 | 8/1974 | Mrozik | 260/556 AR X |
| 3,828,079 | 8/1974 | Mrozik | 260/556 AR X |
| 3,829,487 | 8/1974 | Mrozik | 260/556 AR |
| 3,953,492 | 4/1976 | Mrozik | 260/556 AR X |
| 3,953,493 | 4/1976 | Vanden Heuvel | 260/556 AR X |
| 3,987,199 | 10/1976 | Mrozik | 260/556 AR X |
| 3,997,603 | 12/1976 | Martin | 260/556 AR |
| 4,014,891 | 3/1977 | Goralski et al. | 260/556 AR X |
| 4,035,407 | 7/1977 | Goralski et al. | 260/556 AR X |
| 4,041,073 | 8/1977 | Goralski et al. | 260/556 AR |

FOREIGN PATENT DOCUMENTS 461391 11/1949 Canada .............................. 260/556 AR

*Primary Examiner*—Thomas Waltz
*Attorney, Agent, or Firm*—S. Preston Jones; Richard G. Waterman

[57] ABSTRACT

Compounds are prepared corresponding to the formula

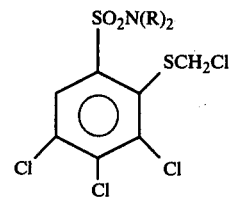

wherein each R represents alkyl of 1 to 4 carbon atoms. These compounds can be employed as starting materials for preparing 3,4,5-trichloro-N,N-di(loweralkyl)-2-(thiomethylthiocyanato)benzenesulfonamides which are useful as antimicrobial agents.

5 Claims, No Drawings

3,4,5-TRICHLORO-N,N-DI(LOWERALKYL)-2-((CHLOROMETHYL)THIO)BENZENESULFONAMIDES

SUMMARY OF THE INVENTION

The present invention is directed to compounds corresponding to the formula

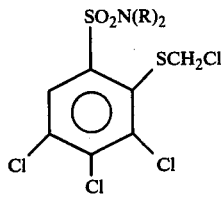

wherein each R represents alkyl of 1 to 4 carbon atoms. These compounds have been found to be useful as intermediates for the preparation of the 3,4,5-trichloro-N,N-di(loweralkyl)-2-(thiomethylthiocyanato)benzenesulfonamides taught in U.S. Pat. No. 4,035,407 issued July 12, 1977. The compounds of the above patent are antimicrobial agents useful for the control of fungal and bacterial organisms such as, for example, bean mildew, *Staphylococcus aureus, Candida albicans, Trichophton mentagrophytes, Bacillus subtilis, Aspergillus terreus, Pullularia pullulans, Mycobacterium phlei,* and *Rhizopus nigricans.*

The compounds of the present invention are crystalline solids which are substantially insoluble in water and are soluble in many common organic solvents.

The term "loweralkyl" as employed in the present specification and claims designates saturated, monovalent aliphatic radicals, including straight and branched chain radicals such as, for example, methyl, ethyl, n-propyl, isopropyl, n-butyl and secondary butyl.

The compounds of the present invention can be prepared by the reaction of 2,3,4-trichloro-6-((di(loweralkyl)amino)sulfonyl)benzenethiol (also known as 3,4,5-trichloro-2-(mercapto)-N,N-di(loweralkyl)benzenesulfonamide) with bromochloromethane, which acts as a (1) reactant and, when employed in excess, also as a (2) solvent. In addition the reaction is conducted in the presence of an alkali metal hydroxide and a quaternary ammonium salt as a catalyst for the reaction. The preparation process as described hereinabove is taught in U.S. Pat. No. 4,014,891 issued Mar. 29, 1977.

As taught in U.S. Pat. No. 4,014,891, the 3,4,5-trichloro-2-(mercapto)-N,N-di(loweralkyl)benzenesulfonamide is converted in situ to the corresponding mercaptide by the action of the alkali metal hydroxide.

Essentially any one of the alkali metal hydroxides can be used in the instant reaction; such as, for example, lithium hydroxide, potassium hydroxide or sodium hydroxide. Currently, sodium and potassium hydroxide are preferred and the most preferred is potassium hydroxide. Such hydroxides are, of course, solid and it is most convenient to use them in a finely divided form (i.e. powdered). Bromochloromethane is a known compound which is normally liquid and boils at 69° C. The stoichiometry of the instant reaction requires one mole of bromochloromethane per mercapto group and it is preferred to employ the bromochloromethane in a substantial excess so that is can also act as the liquid reaction medium.

Additionally, the process is conducted in the presence of a small but catalytic amount of a quaternary ammonium salt having an aggregate carbon content of at least 10 carbon atoms (preferably from about 12 to about 31 carbon atoms). It is noted that such ammonium salts are normally soluble in the bromochloromethane. Examples of such suitable ammonium salts include tetraalkylammonium salts, such as tetra-n-butyl-, tetrahexyl-, tri-n-butylmethyl-, trioctylmethyl- and tridecylmethylammonium chlorides, bromides, bisulfates, tosylates, etc.; aralkyl ammonium salts, such as the tetrabenzyl-, benzyltrimethyl-, benzyltriethyl- and benzyltributylammonium chlorides, bromides, methylsulfates, etc.; aryl ammonium salts, such as triphenylmethylammonium fluoride, chloride or bromide, N,N,N-trimethylanilinium bromide, N,N-diethyl-N-ethylanilinium bisulfate, trimethylnaphthylammonium chloride, p-methylphenyl trimethyl ammonium chloride or tosylate, etc.; 5- and 6-membered heterocyclic compounds containing at least one quaternized nitrogen atom in the ring, such as N-hexylpyridinium iodide, 4-pyridyltriethyl ammonium chloride, N,N-dibutyl morpholinium chloride, etc., and other like compounds.

The preferred ammonium salts are the benzyltrimethyl, benzyltriethyl, tetra-n-butyl and tri-n-butylmethylammonium salts. The most preferred salts are benzyltriethylammonium salts and tetra-n-butylammonium salts.

The ammonium salts are used here in small but catalytic amounts. For example, amounts of from about 0.25 up to about 20 mole percent of the ammonium salt, based on the benzenesulfonamide reactant, have resulted in satisfactory reaction rates.

The instant process is normally conducted in the liquid phase at reaction temperatures of from about 20° to about 65° C. Most often, the reaction proceeds very satisfactorily at ambient temperatures.

DESCRIPTION OF SOME PREFERRED EMBODIMENTS

The following examples serve to illustrate the practice of the present invention but are not intended to be limitations upon the overall scope of the same.

EXAMPLE 1

3,4,5-trichloro-N,N-diethyl-2-((chloromethyl)thio)-benzenesulfonamide

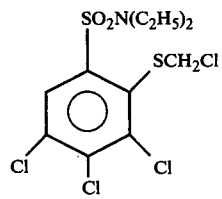

To a slurry of 1.63 grams (0.025 mole) of finely powdered potassium hydroxide (85 percent) in 150 milliliters of bromochloromethane were added 8.72 grams (0.025 mole) of 2,3,4-trichloro-6-((diethylamino)sulfonyl)benzenethiol. To this mixture, 0.40 gram of benzyltriethyl ammonium bromide, was added and the temperature rose from 26° to 30° C. over 20 minutes. The reaction mixture was cooled to room temperature and stirred at this temperature for 2 hours. The reaction mixture was thereafter heated at the reflux temperature of the mixture for 0.5 hour and then cooled to room temperature. The mixture was filtered to remove the potassium bromide by-product produced and then the bromochloromethane was removed from the filtrate, under reduced pressure, leaving a light orange solid as a residue. The residue was recrystallized from diethylether to give 4.2 grams of 3,4,5-trichloro-N,N-diethyl-2-((chloromethyl)thio)benzenesulfonamide as a cream colored solid which melted at 82°-83° C. Hexane was added to the ether filtrate, and the resulting solution concentrated to give an additional 4.1 grams of the desired product. The additional product melted at 81°-82° C. and the combined total yield of the product was 83 percent of theoretical. Upon analysis, the product was found to have carbon, hydrogen, chlorine, nitrogen and sulfur contents of 32.60, 3.17, 35.20, 3.85 and 17.38 percent, respectively, as compared with the theoretical contents of 33.26, 3.30, 35.71, 3.52 and 16.15 percent, respectively, calculated for the above named structure.

By following the procedure of Example 1, the following compounds are made:

1. 3,4,5-trichloro-N,N-dimethyl-2-((chloromethyl)thio)benzenesulfonamide, having a molecular weight of 288.58
2. 3,4,5-trichloro-N,N-di-n-propyl-2-((chloromethyl)thio)benzenesulfonamide, having a molecular weight of 344.69
3. 3,4,5-trichloro-N,N-di-n-butyl-2-((chloromethyl)thio)benzenesulfonamide, having a molecular weight of 372.74

As indicated hereinabove, the 3,4,5-trichloro-N,N-di(loweralkyl)-2-((chloromethyl)thio)benzenesulfonamides of the present invention are useful in preparing 3,4,5-trichloro-N,N-di(loweralkyl)-2-((thiocyanomethyl)thio)benzenesulfonamides. These later compounds can be prepared by the reaction of an appropriate 3,4,5-trichloro-N,N-di(loweralkyl)-2-((chloromethyl)thio)-benzenesulfonamide with an alkali metal thiocyanate in the presence of a reaction medium such as methanol, ethanol, dimethylformamide, acetone or dimethylsulfoxide.

In carrying out this procedure, one molecular equivalent of the 3,4,5-trichloro-N,N-di(loweralkyl)-2-((chloromethyl)thio)benzenesulfonamide in the solvent is mixed with about 1.1 molecular equivalents of an alkali thiocyanate and the resulting mixture is stirred at a temperature of from about room temperature up to the reflux temperature of the mixture for about 0.5 to about 2 hours. After the reaction is complete, the reaction mixture is filtered to remove any insolubles and the solvent removed by evaporation under reduced pressure. The product can be recovered as such or if desired, it can be crystallized from a solvent such as chloroform or hexane or mixtures thereof.

This above procedure can be exemplified as follows:

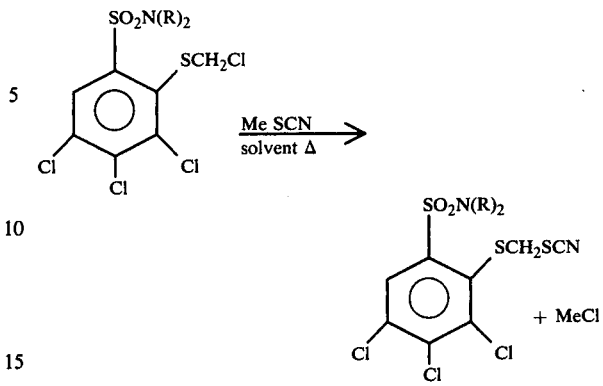

wherein R is as hereinbefore set forth and Me is sodium, potassium or lithium.

By following the above procedure, the compounds of the formula

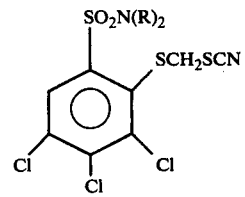

wherein each R represents alkyl of 1 to 4 carbon atoms as taught in U.S. Pat. No. 4,035,407 are prepared. The use of the compounds as active antimicrobial agents is also taught therein.

What is claimed is:

1. A compound corresponding to the formula

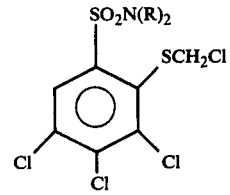

wherein each R represents alkyl of 1 to 4 carbon atoms.

2. The compound as defined in claim 1 which is 3,4,5-trichloro-N,N-dimethyl-2-((chloromethyl)thio)benzenesulfonamide.

3. The compound as defined in claim 1 which is 3,4,5-trichloro-N,N-diethyl-2-((chloromethyl)thio)benzenesulfonamide.

4. The compound as defined in claim 1 which is 3,4,5-trichloro-N,N-di-n-propyl-2-((chloromethyl)thio)benzenesulfonamide.

5. The compound as defined in claim 1 which is 3,4,5-trichloro-N,N-di-n-butyl-2-((chloromethyl)thio)benzenesulfonamide.

* * * * *